(12) United States Patent
Hamasaki et al.

(10) Patent No.: US 9,895,691 B2
(45) Date of Patent: Feb. 20, 2018

(54) ANALYSIS PACKAGE FOR DETECTING PARTICLES IN A SAMPLE LIQUID

(71) Applicant: KABUSHIKI KAISHA TOSHIBA, Minato-ku, Tokyo (JP)

(72) Inventors: Hiroshi Hamasaki, Hiratsuka Kanagawa (JP); Michihiko Nishigaki, Kawasaki Kanagawa (JP); Yutaka Onozuka, Yokohama Kanagawa (JP); Kentaro Kobayashi, Tokyo (JP); Hiroko Miki, Kawasaki Kanagawa (JP); Naofumi Nakamura, Tokyo (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 50 days.

(21) Appl. No.: 14/848,307

(22) Filed: Sep. 8, 2015

(65) Prior Publication Data

US 2016/0231262 A1    Aug. 11, 2016

(30) Foreign Application Priority Data

Feb. 9, 2015    (JP) .................. 2015-023093

(51) Int. Cl.
| | |
|---|---|
| *B01L 3/00* | (2006.01) |
| *G01N 15/12* | (2006.01) |
| *G01N 27/327* | (2006.01) |
| *G01N 33/487* | (2006.01) |

(52) U.S. Cl.
CPC ....... *B01L 3/502715* (2013.01); *B01L 3/5027* (2013.01); *G01N 15/12* (2013.01); *B01L 2200/0647* (2013.01); *B01L 2300/0645* (2013.01); *B01L 2300/0681* (2013.01); *B01L 2300/0816* (2013.01); *B01L 2300/0887* (2013.01); *B01L 2400/0421* (2013.01); *B01L 2400/086* (2013.01); *G01N 27/3273* (2013.01); *G01N 33/48721* (2013.01)

(58) Field of Classification Search
CPC ........................ B01L 3/502715; G01N 27/00
USPC ................................... 324/464–470
See application file for complete search history.

(56) References Cited

U.S. PATENT DOCUMENTS

| | | | |
|---|---|---|---|
| 6,184,523 B1* | 2/2001 | Dowben | H01J 49/482 250/305 |
| 2004/0144658 A1 | 7/2004 | Flory | |
| 2004/0248306 A1* | 12/2004 | Hernandez | B01L 3/5027 436/39 |

(Continued)

FOREIGN PATENT DOCUMENTS

| | | |
|---|---|---|
| JP | 2016024013 A | 2/2016 |
| WO | 2016009674 A1 | 1/2016 |

*Primary Examiner* — Jeff Natalini
(74) *Attorney, Agent, or Firm* — Holtz, Holtz & Volek PC (57) ABSTRACT

According to one embodiment, an analysis package, including a board, an analysis chip provided on the board, the chip including a detector for detecting a particle, a flow channel of a sample liquid, and a liquid receiver of the sample liquid, a first mold layer provided on the analysis chip, the first mold layer including an opening above the liquid receiver, and a second mold layer provided on the board and the first mold layer, the second mold layer including an opening above the opening of the first mold layer, wherein the respective openings of the first and second mold layers are connected above the liquid receiver to allow the sample liquid to be introduced into the liquid receiver from outside.

29 Claims, 9 Drawing Sheets

(56) References Cited

U.S. PATENT DOCUMENTS

| | | |
|---|---|---|
| 2008/0311375 A1 | 12/2008 | Harnack et al. |
| 2009/0069194 A1* | 3/2009 | Ramakrishnan ..... C12Q 1/6851 506/9 |
| 2011/0118132 A1* | 5/2011 | Winger ................... C12Q 1/00 506/7 |
| 2012/0240674 A1* | 9/2012 | Sakuma ................ G01F 1/6845 73/204.25 |
| 2014/0320849 A1* | 10/2014 | Chou ..................... B03C 5/026 356/72 |

* cited by examiner

ANALYSIS PACKAGE FOR DETECTING PARTICLES IN A SAMPLE LIQUID

CROSS-REFERENCE TO RELATED APPLICATIONS

This application is based upon and claims the benefit of priority from Japanese Patent Application No. 2015-023093, filed Feb. 9, 2015, the entire contents of which are incorporated herein by reference.

FIELD

Embodiments described herein relate generally to an analysis package for detecting particles in a sample liquid.

BACKGROUND

In recent years, a microanalysis chip on which microfluidic devices such as microflow channels and detection mechanisms are integrated has been attracting attention in the field of biotechnology and healthcare. In this kind of chip, particles and biopolymers included in a sample liquid can be detected by letting the sample liquid flow in a flow channel and acquiring the displacement of the particles, etc., in the sample liquid as an electrical signal by the variation of electrical resistance.

DETAILED DESCRIPTION

In general, according to one embodiment, an analysis package comprises: a board comprising a wiring layer; an analysis chip provided on the board, the chip comprising a detector for detecting a particle, a flow channel for injecting and ejecting a sample liquid for particle detection to the detector, and a liquid receiver for introducing the sample liquid into the flow channel; a first mold layer provided on the analysis chip, the first mold layer comprising an opening above the liquid receiver; and a second mold layer provided on the board and the first mold layer, the second mold layer comprising an opening above the opening of the first mold layer.

In addition, the respective openings of the first and second mold layers are connected above the liquid receiver to allow the sample liquid to be introduced into the liquid receiver from outside.

analysis packages of embodiments, for instance, microanalysis packages will be described hereinafter with reference to the accompanying drawings.

(First Embodiment)

Figure 1:
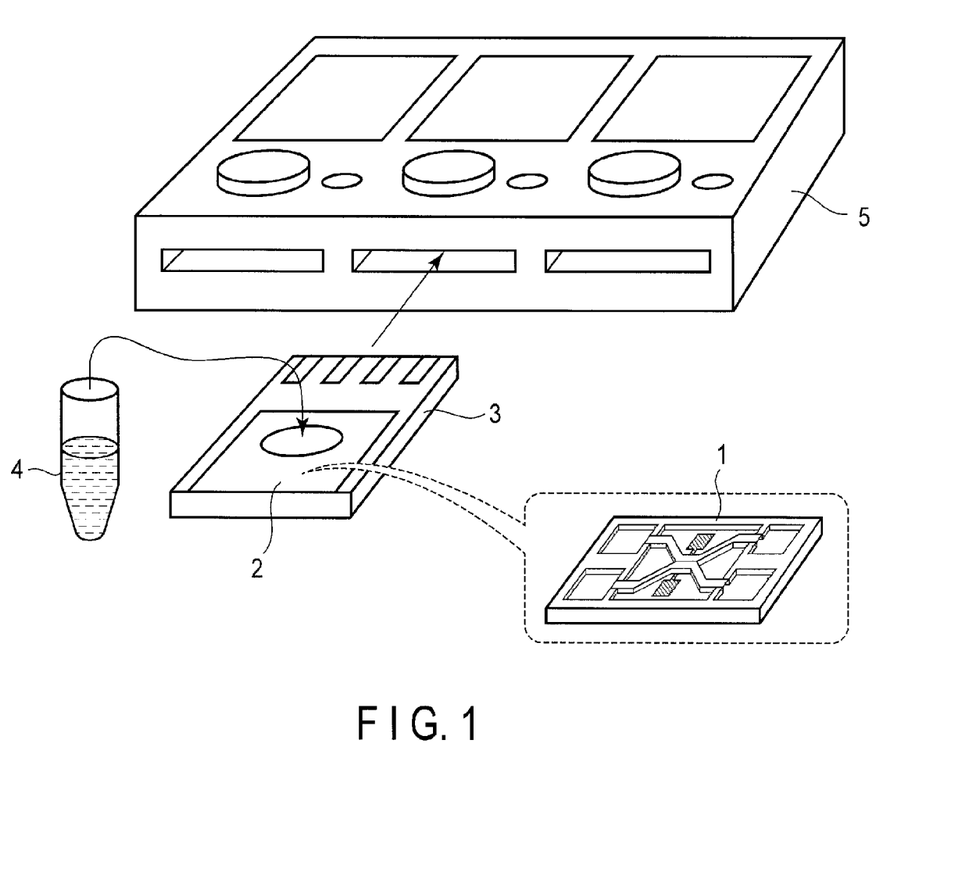
FIG. 1 is a perspective view showing a structure example of a microanalysis system.

FIG. 1 is for explaining a first embodiment, and is a perspective view showing a structure example of a microanalysis system.

An analysis chip, for instance, a semiconductor microanalysis chip 1 does not function alone, and is mounted on a circuit board (board comprising a wiring layer) with a detection IC. In addition, the semiconductor microanalysis chip 1 and the detection IC are molded from resin, etc. A package formed by resin molding is a microanalysis package 2.

The microanalysis package 2 is generally set in a cassette 3 when being used. In addition, the microanalysis package 2 is provided for a test of particles by inserting the cassette 3 into a determination device 5 after dropping a sample liquid 4 onto a necessary portion of the chip 1.

Figure 2:
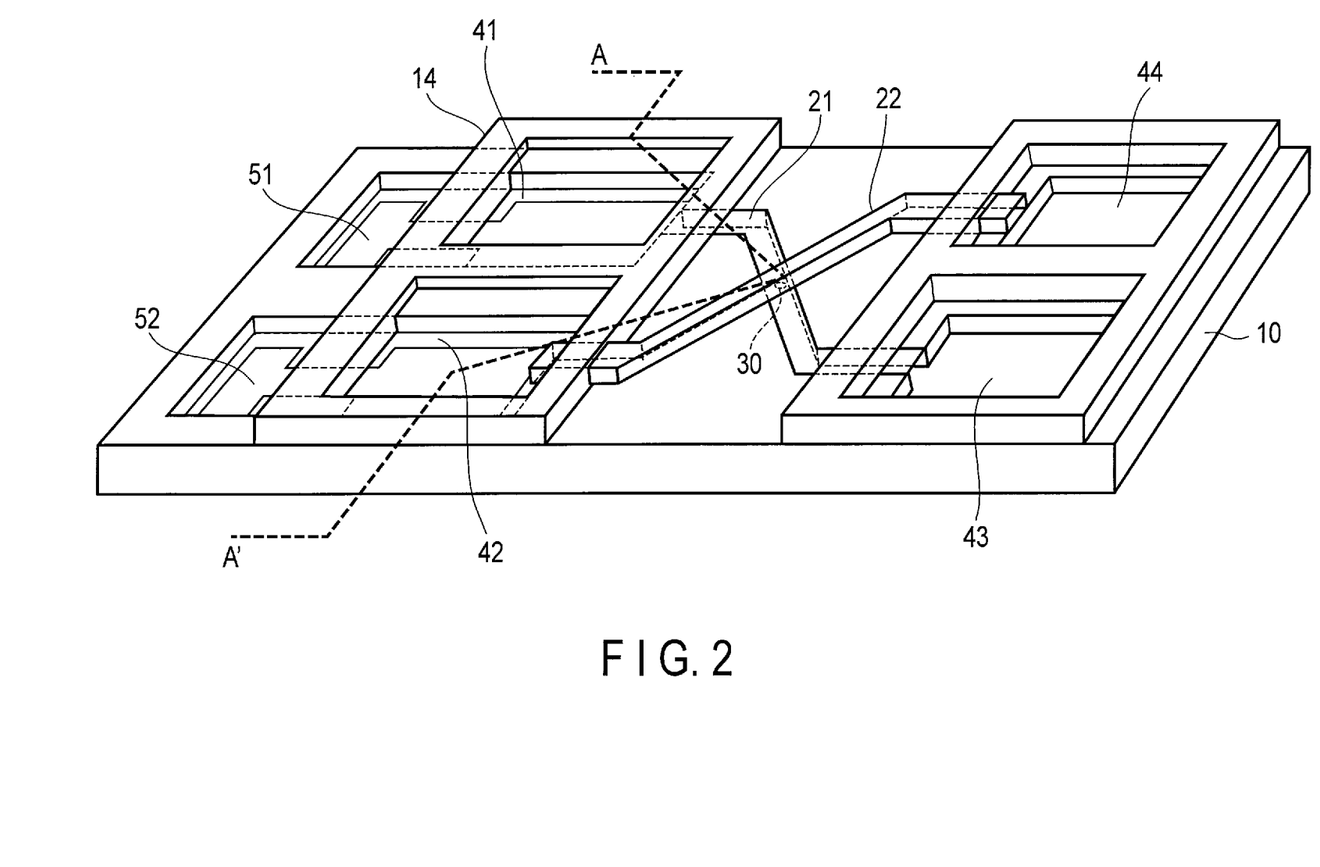
FIG. 2 is a perspective view showing a schematic structure of a semiconductor microanalysis chip used in the microanalysis system of FIG. 1.
Figure 3:
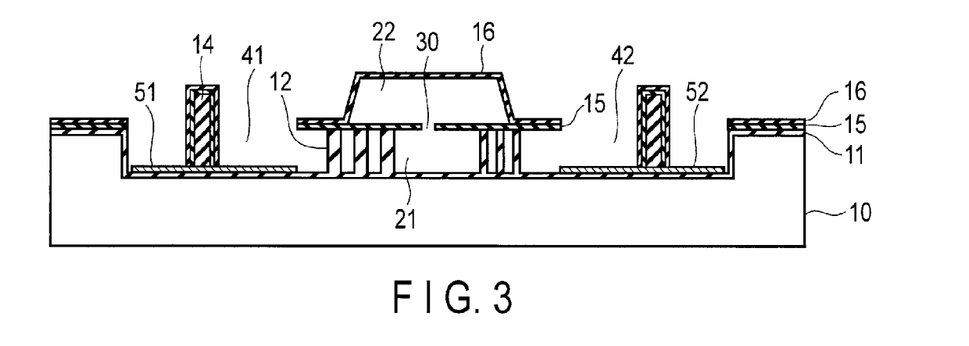
FIG. 3 is a cross-sectional view taken along line A-A' of FIG. 2.

FIG. 2 is a perspective view showing an example of the semiconductor microanalysis chip. FIG. 3 is a cross-sectional view taken along line A-A' of FIG. 2.

The semiconductor microanalysis chip 1 is composed of a semiconductor substrate 10, first and second microflow channels 21 and 22, a microaperture 30 for particle detection, first to fourth reservoirs 41 to 44, and first and second electrodes 51 and 52 formed in the reservoirs 41 and 42. In addition, an insulating film 11 is formed on at least a main surface of the semiconductor substrate 10, and further, insulating films (cap layers) 15 and 16 which cover top surfaces of the microflow channels 21 and 22 are formed.

More specifically, a part of the main surface of the semiconductor substrate 10 is excavated to form the first microflow channel 21 of a substrate excavation type. Moreover, the second microflow channel 22 of an insulating film tunnel type forming a hollow structure of the insulating film 16 is formed on the semiconductor substrate 10 to intersect with the first microflow channel 21. The second microflow channel 22 is formed, not in the semiconductor substrate 10, but on the semiconductor substrate 10. Thus, the second microflow channel 22 is located above the first microflow channel 21. Furthermore, the second microflow channel 22 intersects with the first microflow channel 21 at a central portion of the semiconductor substrate 10, and the microaperture 30 for particle detection is formed at an intersection thereof.

In addition, to form the second microflow channel 22, a pattern of a sacrificial layer is formed in a line on the semiconductor substrate 10, and then, the insulating film 16 is formed to cover the sacrificial layer. Then, a flow channel of an insulating film tunnel type is formed by removing the sacrificial layer. In addition, micro pillars 12 may be disposed in array in the flow channels 21 and 22. These pillars 12 can be formed simultaneously with substrate excavation for the formation of a microflow channel by providing circular masks on a surface of the semiconductor substrate 10. In addition, the pillars 12 accelerate the flow of a sample liquid by capillarity, and function as a filter. That is, the pillars 12 can also function as a filter for preventing a large particle from closing the detection hole 30 by making an interval between the pillars 12 slightly larger than a particle to be detected.

On one end side of the first microflow channel 21, a surrounding bank 14 is formed on the semiconductor substrate 10, whereby the first reservoir (liquid receiver) 41 is formed. It should be noted that the reservoir 41 may be formed by excavating a part of the semiconductor substrate 10 when forming the flow channel. One end of the first microflow channel 21 is connected to the reservoir 41. In addition, the first electrode 51 is formed on the surface of the semiconductor substrate 10 in the first reservoir 41. A part of the electrode 51 is introduced to the outside of the reservoir 41 through a bottom portion of the bank 14.

On one end side of the second microflow channel 22, a surrounding bank 14 is formed on the semiconductor substrate 10, whereby the second reservoir 42 is formed. The second reservoir 42 has substantially the same structure as that of the first reservoir 41, and is connected to the second microflow channel 22. In addition, the second electrode 52 is formed on the surface of the semiconductor substrate 10 in the second reservoir 42. A part of the electrode 52 is introduced to the outside of the reservoir 42 through a bottom portion of the bank 14.

On the other end side of the first microflow channel 21, a surrounding bank 14 is formed on the semiconductor substrate 10, whereby the third reservoir 43 is formed. The structure of the third reservoir 43 is the same as that of the first reservoir 41, except that the electrode 51 is not provided. On the other end side of the second microflow channel 22, a surrounding bank 14 is formed on the semiconductor substrate 10, whereby the fourth reservoir 44 is formed. The structure of the fourth reservoir 44 is the same as that of the reservoir 42, except that the electrode 52 is not provided.

As described above, the first microflow channel 21 connects the first reservoir 41 and the third reservoir 43, and the top surface thereof is covered by the cap layer 15. The second microflow channel 22 connects the second reservoir 42 and the fourth reservoir 44, and the top surface and side surfaces thereof are covered by the cap layer 16.

When a liquid such as a sample liquid is dropped into the first reservoir 41 of the semiconductor microanalysis chip like this, the dropped liquid spreads in the first reservoir 41, and is introduced into the first microflow channel 21. The liquid introduced into the first microflow channel 21 further reaches the third reservoir 43. Similarly, when a liquid such as a sample liquid is dropped into the second reservoir 42, the dropped liquid spreads in the second reservoir 42, and is introduced into the second microflow channel 22. The liquid introduced into the second microflow channel 22 further reaches the fourth reservoir 44.

At this time, the liquid in the first microflow channel 21 is electrically connected to the first electrode 51. Similarly, the liquid in the second microflow channel 22 is electrically connected to the second electrode 52. Moreover, the liquid in the first microflow channel 21 and the liquid in the second microflow channel 22 contact each other through the microaperture 30. Therefore, the first electrode 51 and the second electrode 52 are electrically connected through the dropped liquids.

When a voltage is applied between the first electrode 51 and the second electrode 52 in the state where an electrically conductive sample liquid including a specimen such as particles is dropped into the first reservoir 41 and the second reservoir 42, an ion current flows between the electrodes 51 and 52. That is, an ion current depending on the electrical conductivity of the sample liquid, the sizes and the qualities of materials of the first and second electrodes 51 and 52, the sizes of the first and second microflow channels 21 and 22, the size of the microaperture 30, etc., flows. In addition, an electric field according to the current density of an ion current is produced in the first and second microflow channels 21 and 22 and the microaperture 30, and the electric field intensity is the largest especially in the vicinity of the microaperture 30 which is smaller in size than the first and second microflow channels 21 and 22. Because a surface of a specimen such as particles in a sample liquid is generally electrified, electrophoresis occurs because of this surface charge and the above-described electric field.

In the vicinity of the microaperture 30 where the electric field intensity is high, the movement of particles due to electrophoresis increases, and in some cases, the particles may move from the first microflow channel 21 to the second microflow channel 22 through the microaperture 30, or move in reverse. At this time, because the particles remove a sample liquid in the microaperture 30, the electrical resistance of the microaperture 30 rises, and consequently, the ion current decreases. The amount of change and a time of change in this ion current correspond to the size of a particle passing through the microaperture 30. Therefore, the size of a particle in a sample liquid can be electrically analyzed by measuring the size of an ion current flowing between the first electrode 51 and the second electrode 52.

It should be noted that if particles move from the first flow channel 21 to the second flow channel 22 through the microaperture 30 in one direction, a sample liquid need not be introduced into the second flow channel 22, and an electrolytic solution which enables electrical detection between the electrodes 51 and 52 may be introduced.

In the semiconductor microanalysis chip 1 shown in FIG. 2 and FIG. 3, the microflow channel 22 is an insulating film tunnel type and has a hollow structure, and thus, its mechanical strength is remarkably low. Thus, packaging needs to be performed. On the other hand, because the semiconductor microanalysis chip 1 is a weak current output device, an IC for current-voltage conversion must be mounted close thereto, and the IC is packaged simultaneously with the semiconductor microanalysis chip 1. In this case, if the semiconductor microanalysis chip 1 has a structure as shown in FIG. 2 and FIG. 3 as it is, sufficient mechanical strength cannot be obtained, and thus, the microanalysis chip may be damaged.

Figure 4A:
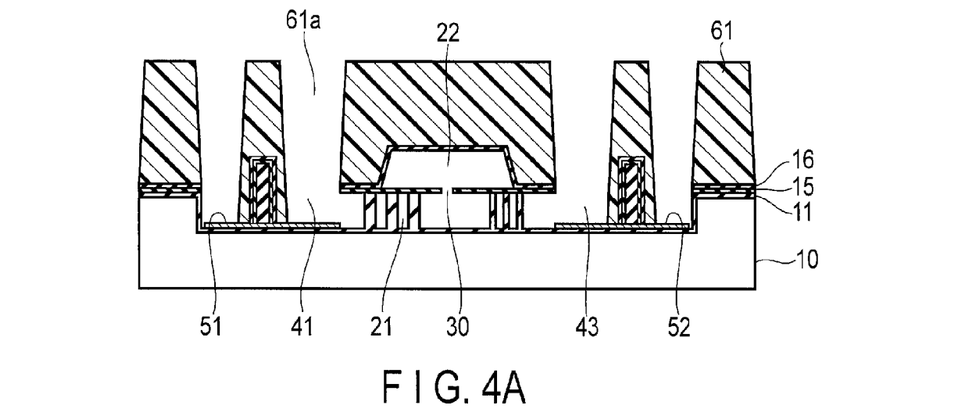
FIGS. 4A and 4B are cross-sectional views showing a manufacturing process of a microanalysis package according to a first embodiment.
Figure 4B:
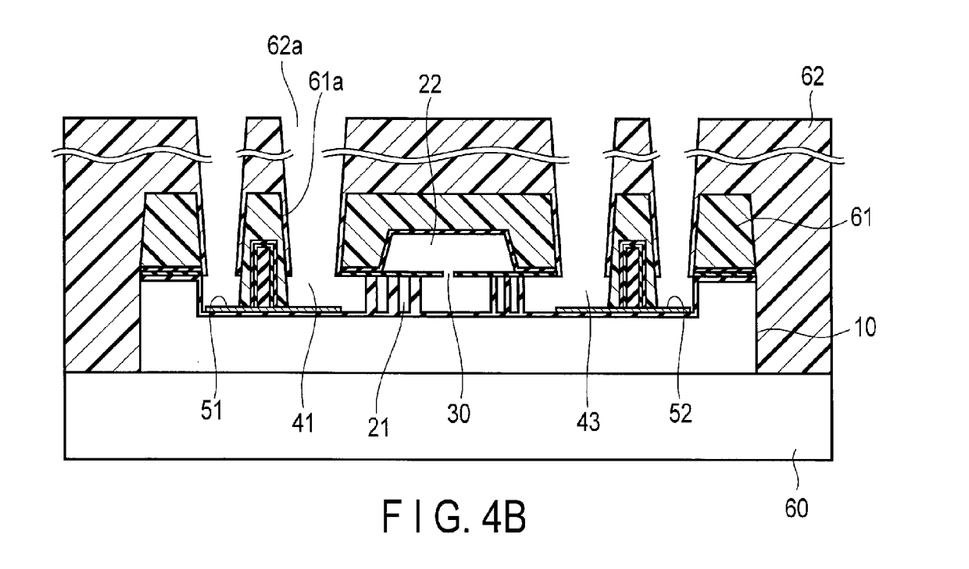

In the present embodiment, therefore, the semiconductor microanalysis chip 1 is packaged in a two-stage mold as shown in FIG. 4A and FIG. 4B.

As shown in FIG. 4A, the semiconductor microanalysis chip 1 is covered by a primary package (first mold layer) 61 composed of polyimide, epoxy resin, silicone resin etc. The first mold layer 61 comprises liquid introduction holes (openings) 61a which connect the reservoirs and the outside. That is, the liquid introduction holes 61a are formed at positions corresponding to the reservoirs 41 to 44 of the mold layer 61, respectively.

The liquid introduction holes 61a can be formed by a semiconductor process such as photolithography by using a photosensitive resin for the first mold layer 61. In this case, a microstructure and high positioning accuracy can be realized, and the liquid introduction holes 61a connected to the respective reservoirs 41 to 44 can be accurately formed.

The semiconductor microanalysis chip 1 on which the first mold layer 61 is formed is mounted on a circuit board 60 as shown in FIG. 4B. Then, the semiconductor microanalysis chip 1 is covered by an external mold (second mold layer) 62 composed of epoxy resin, etc. At this time, liquid injection holes (openings) 62a are formed in the second mold layer 62 above the liquid introduction holes 61a of the first mold layer 61, and the liquid introduction holes 61a of the first mold layer 61 and the liquid injection holes 62a of the second mold layer 62 are connected.

Figure 5:
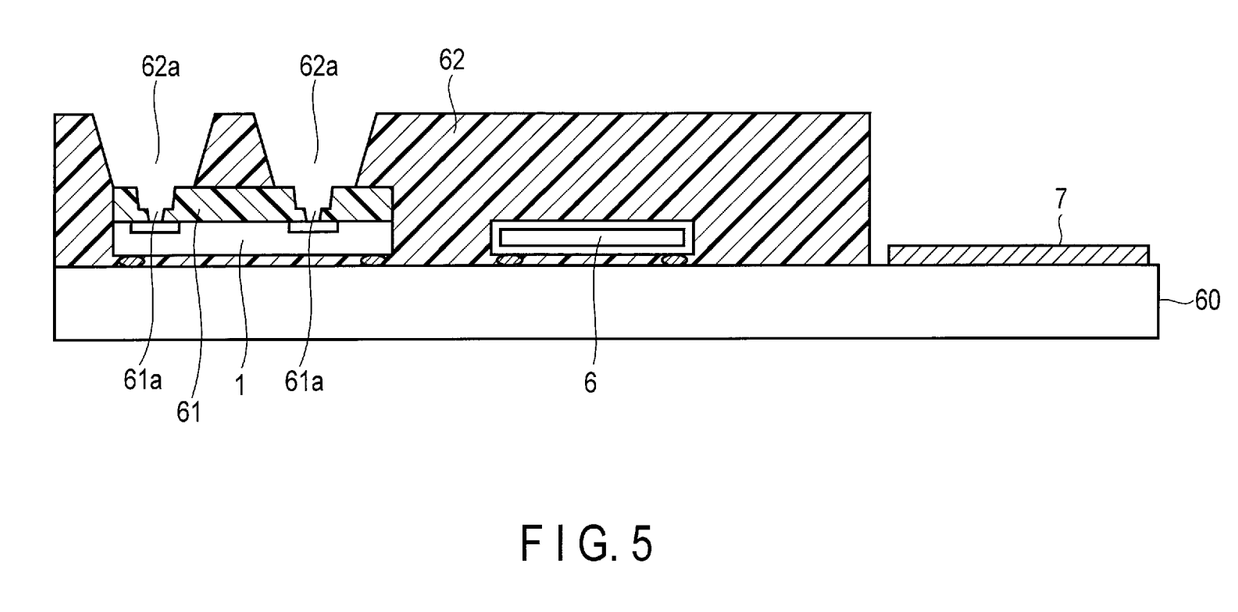
FIG. 5 is a cross-sectional view showing a schematic structure of the microanalysis package according to the first embodiment.

More specifically, an IC 6 for current-voltage conversion is mounted on the circuit board 60 with the semiconductor microanalysis chip 1 as shown in FIG. 5. Moreover, an external electrical connection terminal (electrical signal input/output terminal) 7 is formed on the circuit board 60. In addition, the semiconductor microanalysis chip 1 is covered by the external mold (second mold layer) 62 with the IC 6 for current-voltage conversion.

Here, the liquid injection holes 62a may be formed by etching after the second mold layer 62 is formed. In addition, mask materials or molding pins may be provided on the liquid introduction holes 61a of the first mold layer 61 before the second mold layer 62 is formed, and be removed or ejected after the second mold layer 62 is formed. Moreover, even a mold which has low positional accuracy in forming the second mold layer 62 can surely connect the liquid injection holes 62a to the inner liquid introduction holes 61a by making the liquid injection holes 62a of the second mold layer 62 larger than the liquid introduction holes 61a of the first mold layer 61.

In this manner, in the present embodiment, a primary package is applied to the semiconductor microanalysis chip 1, whereby the semiconductor microanalysis chip 1 can have sufficient mechanical strength at the time of subsequent external molding, and can be packaged without destroying the hollow flow channel. The reliability of the microanalysis package can thereby be improved.

In addition, since a primary package is applied, an advantage that the microanalysis chip alone can be separately tested can also be obtained. Moreover, since the hole diameters of the liquid injection holes 62a of the second mold layer 62 are larger than the hole diameters of the liquid introduction holes 61a of the first mold layer 61, there is also an advantage that even a mold which has low positional accuracy can surely connect the liquid injection holes 62a to the inner liquid introduction holes 61a.

(Second Embodiment)

Figure 6A:
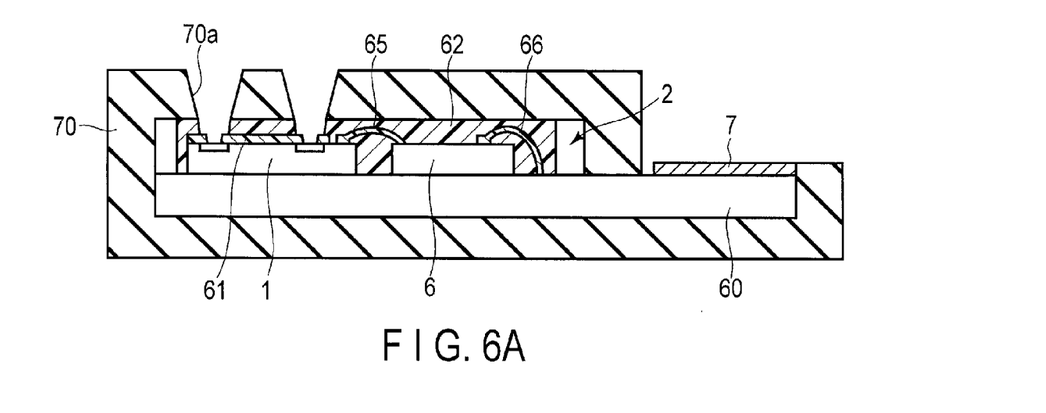
FIGS. 6A to 6C are cross-sectional views showing a schematic structure of a microanalysis package according to a second embodiment.
Figure 6B:
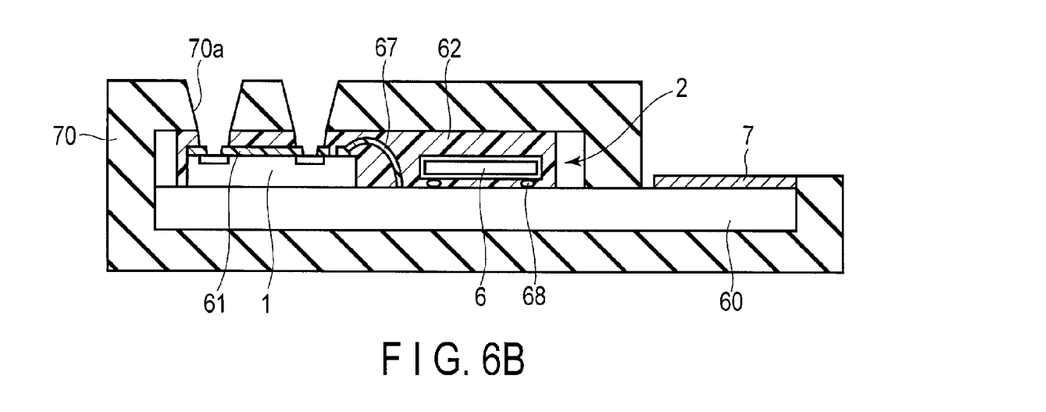
Figure 6C:
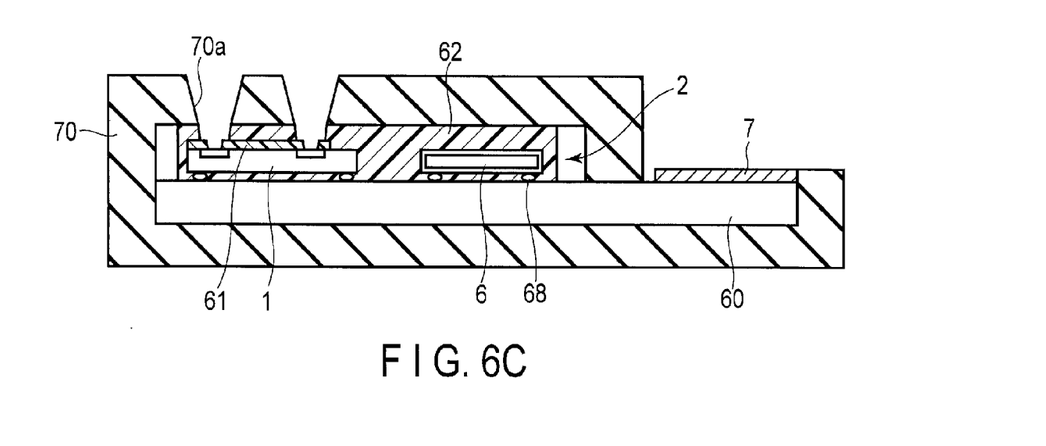

FIGS. 6A to 6C are cross-sectional views showing a schematic structure of a microanalysis package according to a second embodiment. The embodiment is an example in which the positional relationship between electrodes of a semiconductor microanalysis chip or an IC for current-voltage conversion and reservoirs is changed. It should be noted that the same portions as those of FIG. 5 will be given the same numbers as those of FIG. 5, and detailed explanations thereof will be omitted.

FIG. 6A shows the case where electrodes of a semiconductor microanalysis chip 1 and electrodes of reservoirs and an IC 6 are both formed on a top surface. The semiconductor microanalysis chip 1 and the IC 6 are mounted on a circuit board 60. As in the first embodiment, the top surface of the semiconductor microanalysis chip 1 is covered by a first mold layer 61.

The semiconductor microanalysis chip 1 and the IC 6 are electrically connected by a bonding wire 65, and the IC 6 is electrically connected to the circuit board 60 by a bonding wire 66.

A second mold layer 62 are formed on the circuit board 60 on which the semiconductor microanalysis chip 1 and the IC 6 are mounted to cover the semiconductor microanalysis chip 1 and the IC 6. As in the first embodiment, the second mold layer 62 comprises liquid injection holes 62a.

A package obtained by packaging the semiconductor microanalysis chip 1 and the IC 6 is a microanalysis package 2. A housing 70 accommodating the microanalysis package 2 is provided. Openings 70a connected to the liquid injection holes 62a of the second mold layer 62 are provided at parts of the housing 70. In addition, a connection terminal 7 provided on the circuit board 60 is exposed to the outside of the housing 70.

In the above-described structure, the semiconductor microanalysis chip 1 has a simple structure, and parasitic capacitance can be reduced by using the bonding wire 65 for electrical connection to the IC 6 for current-voltage conversion.

FIG. 6B shows the case where the electrodes of the semiconductor microanalysis chip 1 and the reservoirs are on the top surface and the electrodes of the IC are on the bottom surface. The semiconductor microanalysis chip 1 is electrically connected to the circuit board 60 by a bonding wire 67. The IC 6 is electrically connected to the circuit board 60 by pads 68 on a back surface. In this case, because the IC 6 need not be bonded by a wire, the circuit board 60 can be miniaturized.

Figure 7:
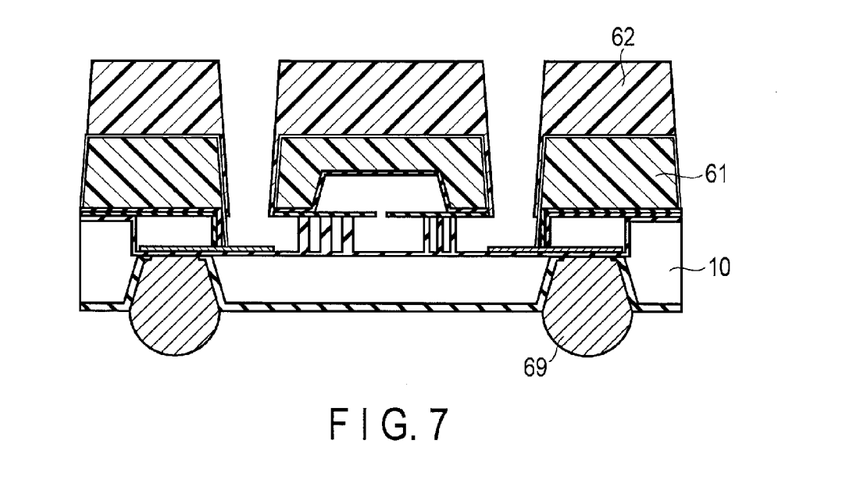
FIG. 7 is a cross-sectional view showing a structure of principal parts of the microanalysis package according to the second embodiment.

FIG. 6C further shows an example in which the electrodes of the semiconductor microanalysis chip 1 are also on the bottom surface. In this case, because wire bonding is unnecessary, further miniaturization can be achieved. It should be noted that in the structure of FIG. 6C, pads 69 which penetrate the semiconductor substrate 10 need to be provided on the back surface of the semiconductor substrate 10 as shown in FIG. 7.

(Third Embodiment)

Figure 8A:
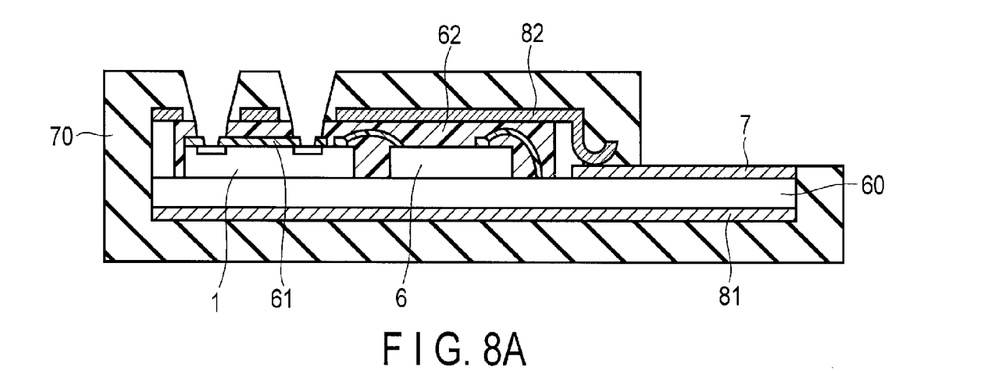
FIGS. 8A and 8B are cross-sectional views showing a schematic structure of a microanalysis package according to a third embodiment.
Figure 8B:
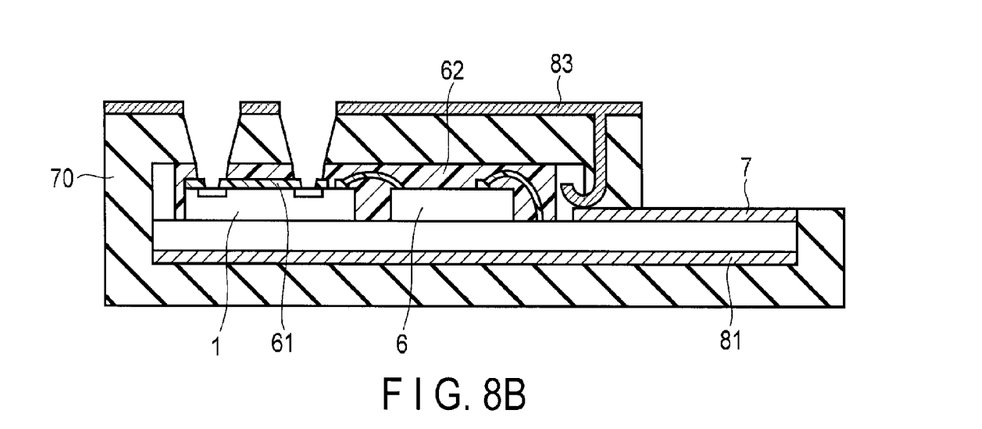

FIGS. 8A and 8B are cross-sectional views showing a schematic structure of a microanalysis package according to a third embodiment. It should be noted that the same portions as those of FIG. 6A to FIG. 6C are given the same numbers as those of FIG. 6A to FIG. 6C, and details explanations thereof will be omitted.

A basic structure in which a semiconductor microanalysis chip 1 and an IC 6 for current-voltage conversion are provided on a circuit board 60 is the same as in the second embodiment. In addition, in FIG. 8A, a first shield metal 81 is provided on a back surface of the circuit board 60, and a second shield metal 82 is provided on a second mold layer 62. The first shield metal 81 and the second shield metal 82 are electrically connected to a connection terminal 7 provided on the circuit board 60 in a housing 70.

In FIG. 8B, the first shield metal 81 is provided on the back surface of the circuit board 60, and a second shield metal 83 is provided on a top surface of the housing 70. The second shield metal 83 penetrates the housing 70, and is electrically connected to the connection terminal 7 provided on the circuit board 60 in the housing 70.

In the above-described structure, in addition to advantages of the first embodiment, the periphery of the semiconductor microanalysis chip 1 is electromagnetically shielded, and thus, the influence of exogenous noise can be removed when particles are detected in the chip 1.

(Fourth Embodiment)

As a fourth embodiment, various examples of a semiconductor microanalysis chip used in the first to third embodiments are first described with reference to FIG. 9A, FIG. 9B, FIG. 10, and FIG. 11.

Figure 9A:
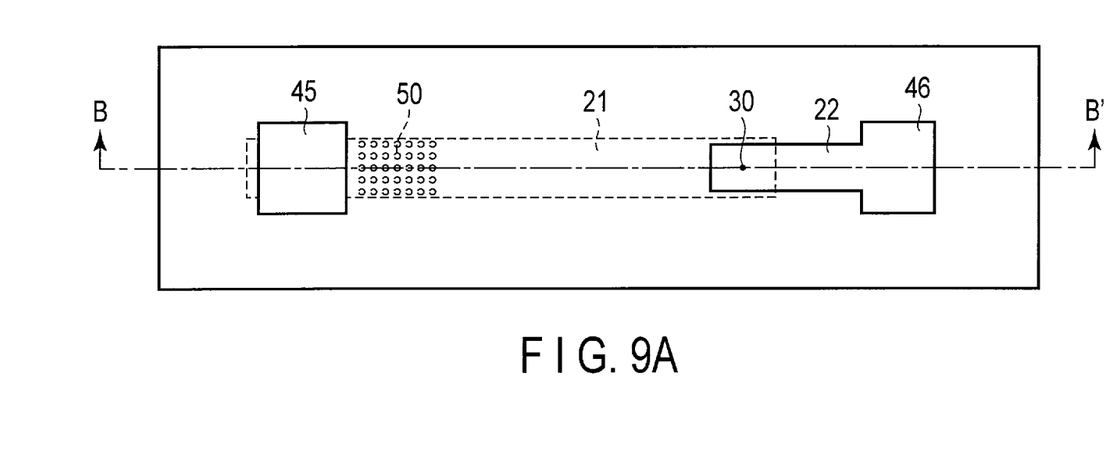
FIG. 9A is a planar view showing an example of the semiconductor microanalysis chip used in the first to third embodiments.
Figure 9B:
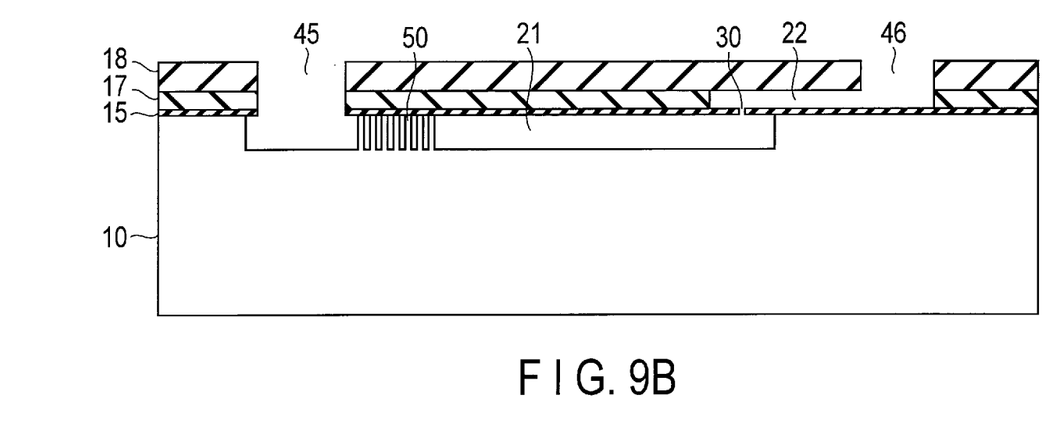
FIG. 9B is a cross-sectional view taken along line B-B' of FIG. 9A.

FIGS. 9A and 9B are illustrations for explaining a schematic structure of a first semiconductor microanalysis chip. FIG. 9A is a plan view, and FIG. 9B is a cross-sectional view taken along line B-B' of FIG. 9A. Here, the uppermost surface in FIG. 9A is shown with a cap layer 18 in FIG. 9B removed.

In this semiconductor microanalysis chip, an insulating film 15, an insulating film 17, and the insulating film 18 are formed in lamination on a semiconductor substrate 10. As the semiconductor substrate 10, for example, Si is used, but other substrates which can be processed in the same way as Si, for example, Ge and SiC, can also be used. In addition, as the insulating films 15, 17, and 18, a dielectric film of $SiO_2$, $Si_3N_4$, $Al_2O_3$, etc., and a polymer material such as polyimide can be used. A first microflow channel 21 is formed by excavating a surface of the Si substrate 10 to a depth of, for example, 2 μm, and one end side of the flow channel 21 is connected to an introduction opening 45 of a sample liquid. On the introduction opening 45 side of the first flow channel 21, a column (pillar) array 50 extending from a bottom surface of the flow channel to a top surface of the flow channel is formed.

The insulating film 15 is formed to cover the first flow channel 21, and in a part thereof, a microaperture 30 is formed. In the insulating film 17, the introduction opening 45, an ejection opening 46, and a second microflow channel 22 are formed. The insulating film 18 is formed to cover the second microflow channel 22, and in parts thereof, the introduction opening 45 and the ejection opening 46 are formed. The microaperture 30 communicates from the top surface of the first microflow channel 21 to a bottom surface of the second microflow channel 22, and the first microflow channel 21 and the second microflow channel 22 are spatially connected through the microaperture 30.

The opening size of the microaperture 30 is slightly larger than a particle to be detected (the maximum diameter of a virus, bacterium, pollen grain, or a compound thereof with other particles). More specifically, the opening size of the microaperture 30 is larger than the outer diameter of a particle to be detected by 5% or more, and is a size which allows a particle to pass through the microaperture by liquid pressure or electrophoresis. In addition, it suffices that the opening size of the microaperture 30 is determined in consideration of how easily a particle to be detected pass therethrough and the sensitivity to change in ion current, which will be described later, and is, for example, 1.5 to 5 times the outer diameter of a particle to be detected.

In the semiconductor microanalysis chip having the above-described structure, when a sample liquid (liquid including particles to be detected) is injected into the introduction opening 45, the sample liquid flows into the first microflow channel 21 by capillarity, and reaches the microaperture 30. As a liquid including particles (specimens) to be detected, a liquid which can be electrified, for example, an electrolytic solution such as a KCl aqueous solution, and various buffer solutions such as a tris ethylene diamine tetra acetic acid (TE) buffer solution and a phosphate buffered saline (PBS) buffer solution, can be used. Then, the second microflow channel 22 is filled with a liquid which can be electrified and does not include sample particles. Particles in a sample liquid move in the flow channel, following the inflow of a sample liquid of the first microflow channel 21 because of capillarity. In this state, electrodes such as metal wires may be inserted into the introduction opening 45 and the ejection opening 46, respectively, as necessary to force sample particles to electrophoretically move by applying a voltage between the electrodes.

Next, electrodes (metal wires, etc.) for observing a current passing through the microaperture 30 are inserted into the introduction opening 45 and the ejection opening 46, respectively, and a voltage is applied to observe an ion current flowing therebetween. When particles are moved by an electric field and pass through the microaperture 30, an opening of the microaperture 30 is shielded if the particles are insulative. Thus, the electrical resistance of an ion current path increases, and an ion current decreases. In contrast, if the particles are electrically conductive and have electron affinity by which a potential barrier with a sample liquid is hardly formed, an increase in ion current may be observed. By observing this change in ion current, it can be detected that the particles have passed through the microaperture 30.

The pillar array 50 extending from the bottom surface of the flow channel to the top surface of the flow channel is disposed in the first microflow channel 21 at appropriate pillar intervals, whereby unnecessary particles large in size are trapped and only particles small in size are allowed to pass downstream. For example, to detect a virus approximately 100 nm in size, a giant particle greater than or equal to 0.5 μm can be prevented from reaching and closing the microaperture 30 by setting the pillar intervals of the pillar array 50 at 250 nm. In addition, the maximum sizes of particles reaching the microaperture 30 can be evened out by appropriately adjusting the pillar intervals and the array length of the pillar array 50. Moreover, because a peak current greater than or equal to a certain change in ion current to be detected can be calculated as a part of noise distribution, detection accuracy can be improved.

In addition, the pillar array 50 can also be formed in the second microflow channel 22 to prevent a dust back current from the ejection opening side, and moreover, a slit-like flow channel array, etc., can also be used instead of the pillar array 50.

Figure 10:
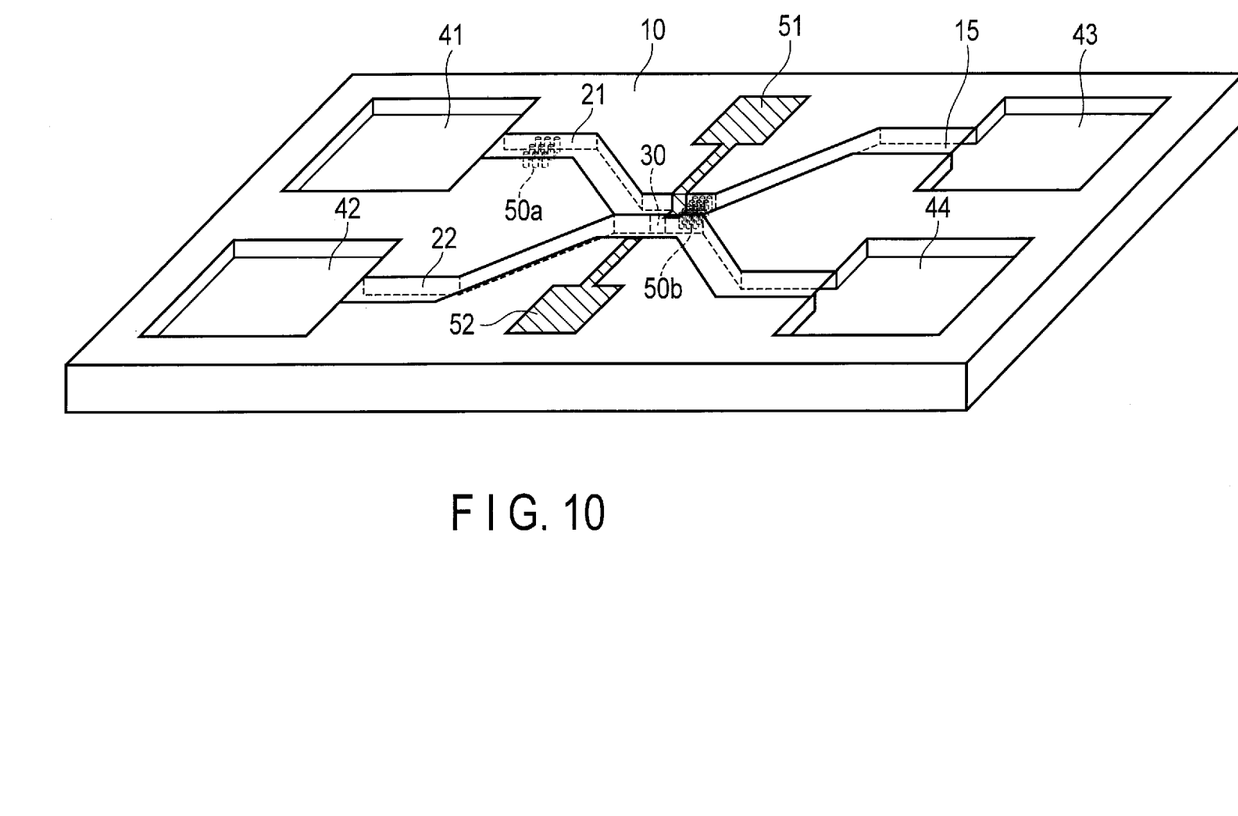
FIG. 10 is a perspective view showing an example of the semiconductor microanalysis chip used in the first to third embodiments.

FIG. 10 is a perspective view showing a schematic structure of a second semiconductor microanalysis chip.

10 in the figure denotes a semiconductor substrate, and as the substrate 10, various semiconductors such as Si, Ge, SiC, GaAs, InP, and GaN can be used.

41 to 44 denote reservoirs for injecting and ejecting a sample liquid: 41 denotes a sample liquid introduction region; 42 denotes an electrolyte solution introduction region; 43 denotes a sample liquid ejection region; and 44 denotes a second electrolyte solution ejection region. These reservoirs 41 to 44 are formed by excavating a surface portion of the Si substrate 10 to a depth of 2 μm, for example, in a pattern of a square with 1 mm sides, for example, by selective etching.

21 denotes a first microflow channel for letting a sample liquid flow, and 22 denotes a second microflow channel for letting an electrolyte solution flow. These microflow channels 21 and 22 are disposed in different layouts, such that parts thereof are close to each other. For example, the microflow channels 21 and 22 are formed by excavating the Si substrate 10 to a width of 50 μm and a depth of 2 μm. Moreover, top portions of the microflow channels 21 and 22 are covered by an insulating thin film (for example, having a thickness of 200 nm) such as a silicon oxide film ($SiO_2$), a silicon nitride film (SiNx), and an alumina film ($Al_2O_3$).

That is, as shown in FIG. 3, a cap layer 15 (lid sealing the flow channels) is formed. Thus, both the first and second microflow channels are trench type tunnel flow channels.

At this time, the cap layer 15 is basically formed toward joints between the reservoirs 41 to 44 and the flow channels. However, the flow channel cap is not formed on at least parts of the joints between the reservoirs 41 to 44 and the flow channels to allow a sample liquid or an electrolyte solution to pass therethrough. Thus, the microflow channels 21 and 22 are tunnel flow channels opening at reservoir portions.

30 denotes a microaperture provided at a contact portion between the first microflow channel 21 and the second microflow channel 22, and is formed by removing a part of a partition 31 (for example, $SiO_2$ having a thickness of 2 μm) between the flow channel 21 and the flow channel 22 by etching in a slit. The size (width) of the microaperture 30 is slightly greater than the size of a particle to be detected, and if the size of a particle to be detected is 1 μmφ, the width of the microaperture 30 is, for example, 1.5 μm.

51 and 52 denote electrodes for detecting particles, and are formed to be exposed to insides of the microflow channels 21 and 22, respectively. As materials for these electrodes, it suffices that surfaces contacting a sample liquid are made of AgCl, Pt, Au, or the like. In addition, the electrodes may not necessarily be integrated as shown in FIG. 10, and particles can also be detected by inserting external electrodes into the reservoirs of the respective flow channels.

An ion current passing through the microaperture 30, that is, a current which flows when the two microflow channels 21 and 22 are filled with an electrolyte solution (solution in which an ion current can flow when an electrolyte is dissolved) and a voltage is applied to the electrodes 51 and 52 (steady-state current which flows when particles are not passing), is basically determined on the basis of the opening size of the microaperture 30. In addition, when particles to be detected pass through the microaperture 30, the particles close a part of the microaperture 30 and block the passage of an ion, and a current decreases accordingly. However, if particles are electrically conductive or can conduct a surface level, the particles receive an ionic charge, and a current may increase because of electrical conduction of the particles themselves. Because this change in ion current is determined on the basis of the relationship between the shapes, the sizes, the lengths, etc., of the microaperture 30 and the particles, the substance of particles passing through the microaperture can be calculated by observing the amount of change, change over time, etc., in ion current.

It suffices that the opening size of the microaperture 30 is determined in consideration of how easily a particle to be detected pass therethrough and the degree of change (sensitivity) in ion current, and is, for example, 1.5 to 5 times the outer diameter of a particle to be detected. In addition, as an electrolyte solution in which particles to be detected are dispersed, for example, an electrolytic solution such as a KCl aqueous solution, and various buffer solutions such as a tris ethylene diamine tetra acetic acid (TE) buffer solution and a phosphate buffered saline (PBS) buffer solution, can be used.

In the semiconductor microanalysis chip like this, particles can be detected only by introduction of a sample liquid and electrical observation. Moreover, the semiconductor microanalysis chip can be microminiaturized and produced on a large scale by semiconductor processing technology, and a particle detection circuit, a discrimination/determination circuit, etc., can be integrated. Thus, a microminiature and supersensitive microanalysis chip can be produced on a large scale at small cost. Accordingly, supersensitive detection of bacteria and viruses can be easily performed, and a contribution can be made to the field of preventing the spread of epidemic diseases and ensuring the safety of food, etc., by application to simple detection of epidemic pathogens and causative bacteria of food poisoning, etc. Such semiconductor microanalysis chips are suitable for uses in the case where a huge amount needs to be provided at extremely small cost, for example, uses for high-speed primary test kits for diseases which need to be dealt with by emergency quarantine, such as a new type of influenza, and simple food poisoning tests in ordinary households.

50a and 50b in the figure denote pillar arrays in microsize which comprise microcolumns (pillars) arranged at regular intervals, and filter particles in a sample liquid according to size through the intervals. As the pillar arrays 50a and 50b, wall (slit) arrays can also be used.

Figure 11:
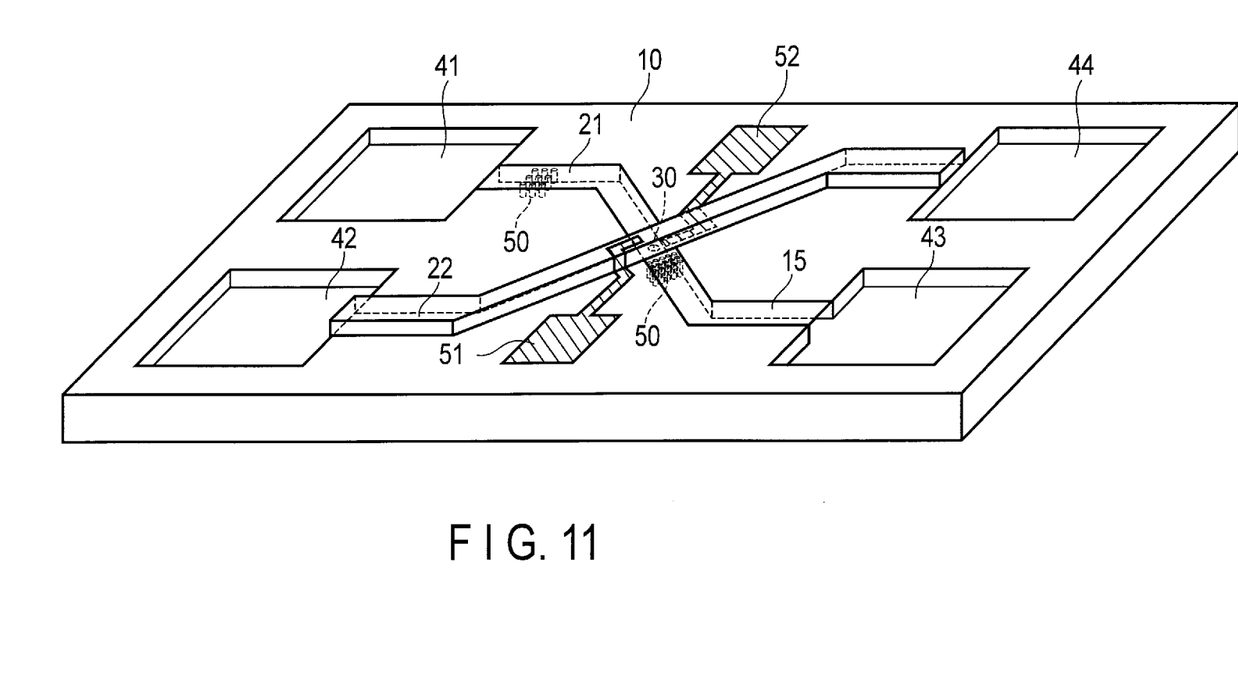
FIG. 11 is a perspective view showing an example of the semiconductor microanalysis chip used in the first to third embodiments.

FIG. 11 is a plan view showing a schematic structure of a third semiconductor microanalysis chip, and shows an example of forming microflow channels 21 and microflow channel 22 in different processes and providing a stack portion (contact portion) at which the two microflow channels 21 and 22 intersect. Here, the flow channels are formed in two stages in which the flow channel 21 to be a sample introduction flow channel is formed on the lower side and the flow channel 22 to be a sample reception flow channel is formed on the upper side. At this time, a microaperture 30 is provided at the stack portion (contact portion) of the two flow channels, and is formed on a partition (cap insulating film of the first flow channel) which is a top surface of the first microflow channel 21 and is a bottom surface of the second microflow channel by photolithography.

In the semiconductor microanalysis chip of FIG. 10, the two microflow channels 21 and 22 are adjacent in a lateral direction with the partition interposed therebetween, the microaperture 30 needs to be formed on the partition vertical to a Si substrate 10, and the slit-like microaperture 30 is formed by patterning a side of the partition. The shape of the microaperture at this time is a quadrangle close to a square if the depth of the flow channels and the width of the microaperture are the same, and is an oblong slit if the depth of the flow channels is greater than the width of the microaperture. Therefore, there has been a problem that when particles pass through the microaperture 30, the opening of the microaperture 30 cannot be sufficiently shielded by the particles, and the change in ion current is less than in the case where the microaperture is circular.

On the other hand, in the semiconductor microanalysis chip of FIG. 11, since the microaperture 30 can be directly patterned and the opening shape of the microaperture 30 can be arbitrarily formed, a circular opening which can shield ionic conduction by particles the most efficiently can be formed. The change in ion current when particles to be detected pass through the microaperture 30 can thereby be maximized, and particles can be detected with higher sensitivity than in the second microanalysis chip.

The first microflow channel 21 is a tunnel flow channel of an excavation type, and the second microflow channel 22 is a flow channel of an insulating film tunnel type. In addition, at the contact portion at which the two flow channels 21 and 22 intersect, the microaperture 30 is formed in the insulating film 15, and the opening shape thereof can be arbitrarily formed. Electrodes which observe an ion current are formed on the bottom surface of the first microflow channel 21 and the top surface of the second microflow channel 22. Higher sensitivity through optimization of the shape of the microaperture can thereby be achieved.

It should be noted that since the two flow channels 21 and 22 are herein disposed to intersect, a sample liquid dropped into a reservoir 41 is ejected to a reservoir 43. As a matter of course, the two flow channels 21 and 22 may also be disposed to turn toward the reservoirs 44 and 43, respectively, at the portion where the two flow channels 21 and 22 stack and contact each other (in this case, a sample liquid dropped into the reservoir 41 is ejected to the reservoir 44).

In the semiconductor microanalysis chip like this, since the two microflow channels 21 and 22 intersect, the microaperture 30 can have a circular opening. Particles can thereby be detected with higher sensitivity.

(Modification)

It should be noted that the present invention is not limited to each of the above-described embodiments.

The structure of a microanalysis chip is in no way limited to those shown in FIG. 2, FIG. 9A, FIG. 9B, FIG. 10, and FIG. 11. It suffices that a detector for detecting a particle, a flow channel for injecting and ejecting a sample liquid for particle detection to the detector, and a liquid receiver for introducing the sample liquid into the flow channel from outside are provided. Moreover, a substrate on which the microanalysis chip is formed is not necessarily limited to a semiconductor substrate, and may be, for example, a material such as quartz obtained by oxidizing the whole semiconductor. In other words, the substrate may be any substrate in which a microflow channel and a microaperture for particle detection can be formed.

If a microanalysis package can have sufficient strength only by a mold, a housing as shown in FIG. 5, FIGS. 6A to 6C, FIGS. 8A, and 8B is not necessarily needed, and can also be omitted. Moreover, the microanalysis package need not necessarily be set in a cassette when being used, and can also be used in a package alone.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An analysis package comprising:
a board comprising a wiring layer;
an analysis chip provided on the board, the chip comprising a detector for detecting a particle, a flow channel for injecting and ejecting a sample liquid for particle detection to the detector, and a liquid receiver for introducing the sample liquid into the flow channel;
a first mold layer provided on the analysis chip to cover the analysis chip, the first mold layer comprising an opening above the liquid receiver; and
a second mold layer provided on the board and the first mold layer to cover the board and the first mold layer, the second mold layer comprising an opening above the opening of the first mold layer,
wherein the first mold layer and the second mold layer are made of different resins, and
wherein the respective openings of the first and second mold layers are connected above the liquid receiver to allow the sample liquid to be introduced into the liquid receiver from outside.

2. The package of claim 1, wherein the opening of the second mold layer is greater in diameter than the opening of the first mold layer.

3. The package of claim 1, wherein the detector is provided at a part of the flow channel, and comprises a microaperture which allows a particle to be detected to pass therethrough and an electrode which allows a voltage to be applied to the sample liquid on an upstream and a downstream side of the microaperture.

4. The package of claim 3, wherein the flow channel comprises an introduction opening on one end side, the introduction opening allowing the sample liquid to be introduced, and the microaperture is provided on the other end side.

5. The package of claim 3, wherein the flow channel comprises first and second flow channels, parts of which contact each other, and the microaperture is provided at a contact portion between the first and second flow channels.

6. The package of claim 3, wherein the flow channel comprises first and second flow channels which overlap or intersect with each other, and the microaperture is provided at an overlap or an intersection of the first and second flow channels.

7. The package of claim 1, further comprising a semiconductor device for detection and an electrical signal input/output terminal provided on the board, to convert a detection result of the detector into an electrical signal,
wherein the second mold layer is provided on the semiconductor device to cover the semiconductor device.

8. The package of claim 1, further comprising:
a first shield metal provided on a back surface of the board; and
a second shield metal provided on an opposite side to the first mold layer of the second mold layer.

9. The package of claim 8, further comprising a housing accommodating the board, the analysis chip, and the respective mold layers,
wherein the second shield metal is provided on a top surface of the housing.

10. The package of claim 1, further comprising pillars provided in the flow channel.

11. The package of claim 1, further comprising a housing to cover the board and the second mold layer.

12. The package of claim 1, wherein:
the second mold layer is provided above and beside the analysis chip,
an upper surface of the analysis chip is covered by the second mold layer with the first mold layer being in between the upper surface of the analysis chip and the second mold layer, and
a side surface of the analysis chip is covered by the second mold layer with the first mold layer not being provided in between the side surface of the analysis chip and the second mold layer.

13. The package of claim 1, wherein:
the first mold layer is provided on an upper surface of the board, and
the second mold layer is provided on an upper surface of the first mold layer and on a side surface of the board and a lower surface of the board.

14. The package of claim 13, wherein the second mold layer is integrally provided on the upper surface of the first mold layer, the side surface of the board, and the lower surface of the board.

15. An analysis package comprising:
a board comprising a wiring layer;
an analysis chip provided on the board, the chip comprising first and second flow channels which overlap or intersect with each other, a microaperture for particle detection provided at an overlap or an intersection of the first and second flow channels, a liquid receiver for introducing a sample liquid into the flow channels, and an electrode which allows a voltage to be applied to the sample liquid on an upstream side and a downstream side of the microaperture;
a first mold layer provided on the analysis chip to cover the analysis chip, the first mold layer comprising an opening above the liquid receiver; and
a second mold layer provided on the board and the first mold layer to cover the board and the first mold layer, the second mold layer comprising an opening above the opening of the first mold layer,
wherein the first mold layer and the second mold layer are made of different resins, and
wherein the respective openings of the first and second mold layers are connected above the liquid receiver to allow the sample liquid to be introduced into the liquid receiver from outside.

16. The package of claim 15, wherein the opening of the second mold layer is greater in diameter than the opening of the first mold layer.

17. The package of claim 15, further comprising a semiconductor device for detection and an electrical signal input/output terminal provided on the board to convert a detection result of the detector into an electrical signal,
wherein the second mold layer is provided on the semiconductor device to cover the semiconductor device.

18. The package of claim 15, further comprising:
a first shield metal provided on a back surface of the board; and
a second shield metal provided on an opposite side to the first mold layer of the second mold layer.

19. The package of claim 18, further comprising a housing accommodating the board, the analysis chip, and the respective mold layers,
wherein the second shield metal is provided on a top surface of the housing.

20. The package of claim 15, wherein:
the second mold layer is provided above and beside the analysis chip,
an upper surface of the analysis chip is covered by the second mold layer with the first mold layer being in between the upper surface of the analysis chip and the second mold layer, and
a side surface of the analysis chip is covered by the second mold layer with the first mold layer not being provided in between the side surface of the analysis chip and the second mold layer.

21. The package of claim 15, wherein:
the first mold layer is provided on an upper surface of the board, and
the second mold layer is provided on an upper surface of the first mold layer and on a side surface of the board and a lower surface of the board.

22. The package of claim 21, wherein the second mold layer is integrally provided on the upper surface of the first mold layer, the side surface of the board, and the lower surface of the board.

23. An analysis package comprising:
a board comprising a wiring layer;
an analysis chip provided on the board, the chip comprising first and second flow channels which overlap or intersect with each other, a microaperture for particle detection provided at an overlap or an intersection of the first and second flow channels, a liquid receiver for introducing a sample liquid into the flow channels, and an electrode which allows a voltage to be applied to the sample liquid on an upstream side and a downstream side of the microaperture;
a first mold layer provided on the analysis chip to cover the analysis chip, the first mold layer comprising an opening above the liquid receiver;
a second mold layer provided on the board and the first mold layer to cover the board and the first mold layer, the second mold layer comprising an opening above the opening of the first mold layer;
a first shield metal provided on a back surface of the board; and
a second shield metal provided on an opposite side to the first mold layer of the second mold layer,
wherein the first mold layer and the second mold layer are made of different resins, and
wherein the respective openings of the first and second mold layers are connected above the liquid receiver to allow the sample liquid to be introduced into the liquid receiver from outside.

24. The package of claim 23, wherein the opening of the second mold layer is greater in diameter than the opening of the first mold layer.

25. The package of claim 23, further comprising a semiconductor device for detection and an electrical signal input/output terminal provided on the board to convert a detection result of the detector into an electrical signal,
wherein the second mold layer is provided on the semiconductor device to cover the semiconductor device.

26. The package of claim 23, further comprising a housing accommodating the board, the analysis chip, and the respective mold layers,
wherein the second shield metal is provided on a top surface of the housing.

27. The package of claim 23, wherein:
the second mold layer is provided above and beside the analysis chip,
an upper surface of the analysis chip is covered by the second mold layer with the first mold layer being in between the upper surface of the analysis chip and the second mold layer, and
a side surface of the analysis chip is covered by the second mold layer with the first mold layer not being provided in between the side surface of the analysis chip and the second mold layer.

28. The package of claim 23, wherein:
the first mold layer is provided on an upper surface of the board, and
the second mold layer is provided on an upper surface of the first mold layer and on a side surface of the board and a lower surface of the board.

29. The package of claim 28, wherein the second mold layer is integrally provided on the upper surface of the first mold layer, the side surface of the board, and the lower surface of the board.

* * * * *